United States Patent [19]
Bryman et al.

[11] Patent Number: 5,886,188
[45] Date of Patent: Mar. 23, 1999

[54] METHOD TO CONVERT 5-CARBOXANILIDO-HALOALKYLTHIAZOLES TO A SINGLE FORM

[75] Inventors: Lois Merle Bryman, North Wales; Enrique Luis Michelotti, Fort Washington; Luong Tu Nguyen, Lansdale, all of Pa.

[73] Assignee: Rohm and Haas Company, Philadelphia, Pa.

[21] Appl. No.: 872,406

[22] Filed: Jun. 10, 1997

[51] Int. Cl.$^6$ .......................... C07D 277/54; A01N 43/78
[52] U.S. Cl. ............................................. 548/200; 514/365
[58] Field of Search ............................... 548/200; 514/365

[56] References Cited

U.S. PATENT DOCUMENTS 3,725,427  4/1973  Harrison et al. .................... 260/302
5,045,554  9/1991  Alt et al. ............................ 514/365

FOREIGN PATENT DOCUMENTS

WO97/31908  4/1997  Japan.

*Primary Examiner*—Mukund J. Shah
*Assistant Examiner*—Ann Kessinger
*Attorney, Agent, or Firm*—Thomas D. Rogerson The present invention relates to a method for converting 5-carboxanilido-haloalkylthiazoles having mixed structural forms into a single structural form. The invention also provides single-structural form 5-carboxanilido-haloalkylthiazoles, compositions of the single-structural form 5-carboxanilido-haloalkylthiazoles, and methods to formulate such compounds.

6 Claims, No Drawings

METHOD TO CONVERT 5-CARBOXANILIDO-HALOALKYLTHIAZOLES TO A SINGLE FORM

This is a nonprovisional application of prior provisional application Ser. No. 60/038,487 filed Feb. 24, 1997, now abandoned.

The present invention relates to a method for converting 5-carboxanilido-haloalkylthiazoles having mixed structural forms into a single structural form. The invention also provides single-structural form 5-carboxanilido-haloalkylthiazoles and methods to formulate such compounds.

U.S. Pat. No. 5,045,554 discloses a class of substituted 5-carboxanilidothiazoles having the general formula I:

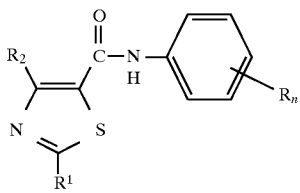

which are useful for controlling plant fungus disease such as, for example Basidiomycetes such as Rhizoctonia, Sclerotium, and Corticium, as well as Alternaria and Spirothica. We have discovered that when such compounds are manufactured, the technical grade of the compound exists as a mixture of at least two different forms of the compound. These different forms have the same structural formula but apparently differ in the spatial orientation of the various substituent groups. As a consequence, the technical grade compound may exist in two or more different crystalline forms. The forms can be distinguished by differences in the position of their characteristic endothermic peak when analyzed using differential scanning calorimetry. The ratio of forms typically ranges from 3:1 to 5:1 and averages about 4:1. Because of the presence of more than one form of the compound, the technical grade product has characteristics similar to that of an impure mixture. The problem with having an "impurity" in the product is that often such mixtures are more difficult to formulate than if the product exists in a single form. Thus, there is a continuing need for technical grade products which exist in only one form. This invention provides a method to convert products containing more than one form into final products containing only one form.

The method of this invention comprises the steps of:
a) forming a basic solution by dissolving a compound of the formula:

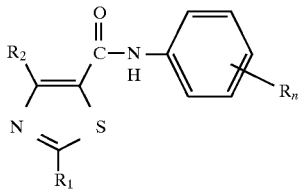

wherein $R_1$ is selected from $(C_1-C_2)$haloalkyl and $(C_1-C_5)$alkyl;
$R_2$ is selected from $(C_1-C_5)$alkyl and $(C_1-C_2)$haloalkyl;
provided that at least one of $R_1$ and $R_2$ is a $(C_1-C_2)$haloalkyl;
n is from one to five, each R is an independently selected electron withdrawing group; and wherein the compound is present in more than one form;
in a solvent by contacting the compound with one or more equivalents of a base, based on the equivalents of compound present; and
b) precipitating a single form of the compound by combining an acid with the basic solution.

Preferably $R_1$ is a $(C_1-C_2)$alkyl, most preferably methyl; $R_2$ is a $(C_1-C_2)$haloalkyl, preferably halomethyl, more preferably perhalomethyl, most preferably trifluoromethyl. Preferably n is two to four, most preferably three to four. Preferably, the R groups are located in the ortho or para positions and most preferably in the ortho positions. Preferably the para substituent, if any, also has lipophilic character. Each R group is preferably independently selected from halo (preferably chloro, bromo, or iodo), halo$(C_1-C_5)$alkyl (preferably halo$(C_1-C_2)$alkyl, more preferably perhalomethyl or trifluoromethyl), or halo$(C_1-C_5)$alkoxy (preferably halo$(C_1-C_2)$alkoxy, more preferably perhalomethoxy or trifluoromethoxy). Other suitable R groups include nitro, cyano, pentahalosulfur preferably pentafluorosulfur), halomethylthio, haloethylthio, $(C_1-C_2)$alkylsulfinyl, halo$(C_1-C_2)$alkylsulfinyl, $(C_1C_2)$alkylsulfonyl, and halo$(C_1-C_2)$alkylsulfonyl. Haloethyl, haloethoxy, haloethylthio, haloethylsulfinyl, and haloethylsulfonyl electron withdrawing substituents preferably have at least one halo substituent on the 1-carbon atom and most preferably two halo substituents on the 1-carbon atom. A preferred compound of this invention is 5-(2,6-dibromo-4-trifluoromethoxycarboxanilido)-2-methyl-4-trifluoromethyl-1,3-thiazole, known under the common name thifluzamide.

The base may be any organic or inorganic base which will abstract at least one proton from the compound of formula I and which is soluble in the solvent. Preferably the base has a $pK_a$ of 10 or more. Preferable bases include alkaline and alkaline earth hydroxides; most preferably sodium, potassium, and ammonium hydroxides:

The solvent may be any polar solvent or solvent mixture in which the acid, the base, and the base salt of the compound are soluble but in which the compound itself is not soluble. Aqueous solvents are preferred. Water is most preferred. Different solvents may be used in the various steps of the method, keeping in mind the relative solubilities of the compound, the acid, the base, and the various salts which will be present.

The method may be carried out at a variety of temperatures, depending upon the relative solubilities of the salt and the final product. Preferably the process is carried out at from 5° to 100° C. Most preferably from 40° to 60° C. The temperatures of the various steps of the process need not be the same.

The acid may be any inorganic or organic acid which is soluble in the base solution and also soluble in the solution after precipitation of the final product. Preferably the acid is dissolved in a solvent, preferably water. Inorganic mineral acids are preferred. Most preferred is aqueous hydrochloric acid.

The precipitation step may also be carried out in a variety of ways. The base solution may be added to the acid. The acid may be added to the base solution. Preferably, both the acid and the base solution are simultaneously added to a third solvent, which need not be the same solvent as that used in the base solution or the acid. On a large scale, it is preferable to add the basic solution to the acid. The temperature of the precipitation reaction is preferably carried out between 5° and 100° C. It need not be the same temperature as the first step.

In a second embodiment, this invention provides compounds of formula I wherein the compound is in a single form. A third embodiment of this invention provides compositions comprising compounds of formula I and an agronomically acceptable carrier.

A further embodiment of this invention is a method to prepare a formulation of a compound of formula I wherein the compound is in a single form; comprising the steps of:

a) forming a basic solution by dissolving a compound of the formula:

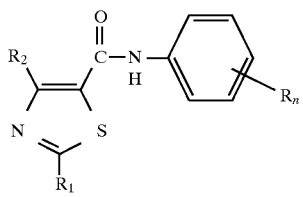

wherein $R_1$ is selected from $(C_1-C_2)$haloalkyl and $(C_1-C_5)$alkyl;

$R_2$ is selected from $(C_1-C_5)$alkyl and $(C_1-C_2)$ haloalkyl;

provided that at least one of $R_1$ and $R_2$ is a $(C_1-C_2)$ haloalkyl;

n is from one to five, each R is an independently selected electron withdrawing group; and wherein the compound is present in more than one form;

in a solvent by contacting the compound with one or more equivalents of a base, based on the equivalents of compound present;

b) precipitating a single form of the compound by combining an acid with the basic solution in the presence of one or more agronomically acceptable carriers.

We have discovered that this method allows the simultaneous conversion of the form of the compound to a single form and formulation of the compound. This provides a distinct advantage over the usual process of manufacturing and isolating the active ingredient and then formulating the active ingredient in a subsequent process. The compound may be used either dry or as manufactured as a wet cake material, that is, containing water from prior processing steps. The formulation ingredients may be present in the basic solution, combined with the acid, or present in a third container into which both the basic solution and the acid are added simultaneously, sequentially, or stepwise. The formulation ingredients may also be divided among any two or three of these. Preferably, the basic solution is added to the acid which is in solution with the majority of the formulation ingredients. Such formulations are suitable for use directly or may be further formulated into other formulations.

Substituted 5-carboxanilidothiazole compounds are prepared by known procedures, including those disclosed in U.S. Pat. No. 5,045,554 (see particularly columns 4–15) by reacting an appropriately substituted thiazole having a 5-carbonylchloride substituent with an appropriately substituted aniline in suitable solvent(s) at an elevated temperature.

Formulations of the compound are prepared by admixing the compound with one or more agonomically acceptable carriers. The term "agronomically acceptable carrier" means any substance which can be used to aid the dispersion of the compound in a pesticide composition in water without impairing the compound's effectiveness and which by itself has no significant detrimental effect on the soil, equipment, desirable plants, or the agronomic environment. Such carriers include adjuvants, diluents, extenders, carriers, surfactants, conditioning agents, antifreezes, antifoaming agents, thickeners, wetting agents, spreading agents, dispersing agents, stickers, adhesives, emulsifying agents, and the like to provide compositions in the form of particulate solids, solutions, dispersions, or emulsions. Such adjuvants commonly used in the art can be found in the John W. McCutcheon, Inc. publication Detergents and Emulsifiers, Annual, Allured Publishing Company, Ridgewood, N.J., U.S.A Such compositions include, for example, wettable powders, granulars, dusts, emulsifiable concentrates, and flowables.

Differential Scanning Calorimetry (DSC)—Apparatus and Method

DSC analysis was conducted using a TA Instruments 2920 Differential Scanning Calorimeter, Part #915001-902, Serial # MA2920-301, or a TA Instruments 2010 Differential Scanning Calorimeter. The analysis used a 10° C./min. temperature ramp to 200° C. The sample was contained in standard aluminum crimped autosampler pans. Purge gas was nitrogen at a flow of 50 ml/min.

EXAMPLE 1

Process for Preparing Thifluzamide with a Single Form

Technical grade thifluzamide (100 g., approximately 98% pure) was added with stirring to a 500 ml flask containing 150 ml of 8% aqueous sodium hydroxide. The resulting mixture was stirred an additional 30 minutes, and then filtered. The solids were discarded, and the filtrate was slowly added to 300 ml of 6% aqueous hydrochloric acid producing a precipitate. The resulting mixture was stirred at room temperature for 30 minutes and then filtered. The solid filter cake was washed twice with 150 ml of cold water and dried yielding 95 g of thifluzamide final product.

The starting technical grade thifluzamide showed endothermic peaks at 133.35° C. (0.1273 cal/g), 154.86° C. (2.850 cal./g), and 174.04° C. (10.92 cal/g). Differential scanning calorimetry of the thifluzamide final product showed a single endothermic peak at 176.72° C.

EXAMPLE 2

Simultaneous Preparation of Thifluzamide in a Single Form and Formulation

The following three solutions were prepared:

| | Material | % | Moles | Equivalent |
|---|---|---|---|---|
| Part A | Thifluzamide (96% AI) | 24.00 | 0.043 | 1.0 |
| | Sodium Hydroxide (50%) | 4.12 | 0.052 | 1.2 |
| | Water | 20.00 | — | — |
| | Antifoam* | 0.30 | — | — |
| Part B | Hydrochloric Acid (37%) | 5.13 | 0.052 | 1.2 |
| | Propylene Glycol | 6.00 | — | — |
| | Antifoam* | 0.30 | — | — |
| | Surfactant A | 3.00 | — | — |
| | Surfactant B | 2.00 | — | — |
| | Water | 34.85 | — | — |
| Part C | Thickener | 0.30 | — | — |
| | Total | 100.0% | | |

*Antifoam = Antifoam C ™; Dow Corning Company
*Surfactant A = Atlox ™ 4913, Imperial Chemical Industries -continued

| Material | % | Moles | Equivalent |
|---|---|---|---|

*Surfactant B = Atsurf ™ 311, Imperial Chemical Industries
*Thickener = Kelzan ™ S, Monsanto Company All part A ingredients were mixed in a separate flask. All ingredients in part B were mixed well in a formulation flask equipped with strong agitator. While agitating the mixture B strongly, part A was added dropwise over a 30 min period. The formulation flask temperature increased to 40° C. during the addition. After the addition of part A was completed, part C was added slowly. The mixture was then homogenized for additional 30 min. The resulting suspension concentrate had a mean particle size for the thifluzamide of 3.2 microns.

DSC Analysis:

To confirm that the thifluzamide in the suspension concentrate was in a single form, a 10 gram sample was diluted and mixed well with 250 ml of tap water in a volumetric cylinder. After 4 days settling at room temperature the mixture separated into a top liquid phase and a solid bottom phase. The top liquid phase was removed, fresh water was added and the above process was repeated. The top liquid phase was removed and the solid bottom material was transferred onto a drying pan. The pan was placed in an 80° C. oven overnight. The dried solid was collected (2.0 g, 87% recovery) and analyzed by DSC analysis. The DSC analysis showed a single endothermic peak at 177.59° C.

We claim:

1. A method, comprising the steps of:

a) forming a basic solution by dissolving a compound of the formula:

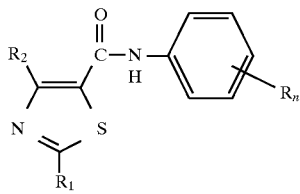

wherein $R_1$ is selected from $(C_1-C_2)$haloalkyl and $(C_1-C_5)$alkyl; $R_2$ is selected from $(C_1-C_5)$alkyl and $(C_1-C_2)$haloalkyl; provided that at least one of $R_1$ and $R_2$ is a $(C_1-C_2$ )haloalkyl; n is from one to five, each R is independently halo, halo($C_1-C_5$)alkyl, halo($C_1-C_5$)alkoxy, nitro, cyano, pentahalosulfur, halo($C_1-C_2$)alkylthio, ($C_1-C_2$)alkylsulfinyl, halo ($C_1-C_2$)alkylsulfinyl, ($C_1-C_2$)alkylsulfonyl, or halo ($C_1-C_2$)alkylsulfonyl; and wherein the compound is present in more than one form and has more than one endothermic peak by differential scanning calorimetry in a solvent by contacting the compound with one or more equivalents of a base, based on the equivalents of compound present; and b) precipitating a single form of the compound by combining an acid with the basic solutions, wherein the single form of the compound has one endothermic peak by differential scanning calorimetry.

2. The method of claim 1, comprising the steps of:

a. forming a basic solution by dissolving a compound of the formula:

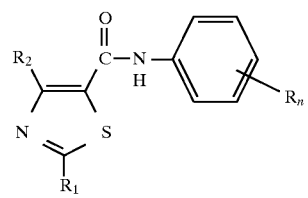

wherein:

each R is independently selected from chloro, bromo, iodo, halo($C_1-C_5$)alkyl, halo($C_1-C_5$)alkoxy, nitro, cyano, halomethylthio, haloethylthio, ($C_1-C_2$) alkylsulfinyl, halo($C_1-C_2$)alkylsulfinyl, ($C_1-C_2$) alkylsulfonyl, and halo($C_1-C_2$)alkylsulfonyl;

$R_1$ and $R_2$ are each independently selected from ($C_1-C_5$)alkyl and ($C_1-C_2$)haloalkyl, provided that at least one of $R_1$ and $R_2$ is selected from ($C_1-C_2$) haloalkyl; and n is from 2 to 4; and wherein the compound is present in more than one form and has more than one endothermic peak by differential scanning calorimetry; and b. precipitating a single form of the compound by combining an acid with the basic solution wherein the single form of the compound has one endothermic peak by differential scanning calorimetry.

3. The method of claim 2, comprising the steps of:

a. forming a basic solution by dissolving a compound of the formula:

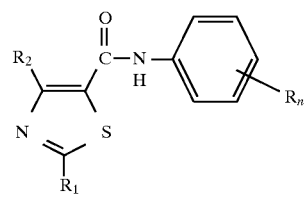

wherein:

each R is independently selected from chloro, bromo, and halo($C_1-C_5$)alkoxy;

$R_1$ is methyl;

$R_2$ is halomethyl; and n is 3; and wherein the compound is present in more than one form and has more than one endothermic peak by differential scanning calorimetry; and b. precipitating a single form of the compound by combining an acid with the basic solution, wherein the single form of the compound has one endothermic peak by differential scanning calorimetry.

4. The method of claim 3 wherein the compound of the composition is 5-(2,6-dibromo-4-trifluoromethoxycarboxanilido)-2-methyl-4-trifluoromethyl-1,3-thiazole.

5. A method to prepare a formulation of a compound wherein the compound is in a single form; comprising the steps of:

a) forming a basic solution by dissolving a compound of the formula:

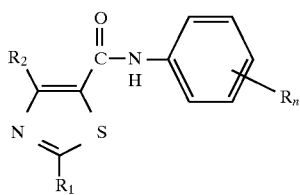

wherein $R_1$ is selected from $(C_1-C_2)$haloalkyl and $(C_1-C_5)$alkyl; $R_2$ is selected from $(C_1-C_5)$alkyl and $(C_1-C_2)$haloalkyl; provided that at least one of $R_1$ and $R_2$ is a $(C_1-C_2)$haloalkyl; n is from one to five, each R is independently halo, halo$(C_1-C_5)$alkyl, halo$(C_1-C_5)$alkoxy, nitro, cyano, pentahalosulfur, halo$(C_1-C_2)$alkylthio, $(C_1-C_2)$alkylsulfinyl, halo $(C_1-C_2)$alkylsulfinyl, $(C_1-C_2)$alkylsulfonyl, or halo $(C_1-C_2)$alkylsulfonyl; and wherein the compound is present in more than one form and has more than one endothermic peak by differential scanning calorimetry;

in a solvent by contacting the compound with one or more equivalents of a base, based on the equivalents of the compound present;

b) precipitating a single form of the compound, wherein the single form of the compound has one endothermic peak by differential scanning calorimetry, by combining an acid with the basic solution in the presence of one or more agronomically acceptable carriers.

6. The method of claim 5 wherein the agronomically acceptable carrier is selected from one or more adjuvants, diluents, extenders, carriers, surfactants, conditioning agents, antifreezes, antifoaming agents, thickeners, wetting agents, spreading agents, dispersing agents, stickers, adhesives, and emulsifying agents.

* * * * *